United States Patent [19]
Rennick

[11] Patent Number: 5,368,854
[45] Date of Patent: Nov. 29, 1994

[54] USE OF IL-10 TO TREAT INFLAMMATORY BOWEL DISEASE

[75] Inventor: Donna Rennick, Los Altos, Calif.

[73] Assignee: Schering Corporation, Kenilworth, N.J.

[21] Appl. No.: 932,900

[22] Filed: Aug. 20, 1992

[51] Int. Cl.$^5$ ............................................. A61K 45/05
[52] U.S. Cl. .................................................... 424/85.2
[58] Field of Search ....................................... 424/85.2

[56] References Cited

PUBLICATIONS

Malefyt et al. J. Exp. Med. vol. 174 (Nov. 1991) pp. 1209–1220.
Peppercorn, Mark A. (1990) "Advances in Drug Therapy for Inflammatory Bowel Disease", *Annals of Internal Medicine*, 112:50–60.
Hanauer, Stephen B., et al. (1991) "Risk–Benefit Assessment of Drugs Used in the Treatment of Inflammatory Bowel Disease", *Drug Safety* 6 (3):192–219.
Linn, Frank V., et al. (1992) "Drug Therapy for Inflammatory Bowel Disease: Park I", *The American Journal of Surgery*, 164:85–89.
Linn, Frank V., et al. (1992) "Drug Therapy for Inflammatory Bowel Disease: Part II", *The American Journal of Surgery*, 164:178–185.
Grob, et al. "Inflammatory Mediators in Chronic Inflammatory Bowel Diseases", *Klinische Wochen schrift*, vol. 69, pp. 981–987, Apr. 24, 1991.
Apgar, et al., "Newer Aspects of Inflammatory Bowel Disease and its Cutaneous Manifestations: A Selective Review," *Seminars in Dermatology*, vol. 10, No. 3, pp. 138–147, Sep., 1991.
Goodnow, Christopher, C., "Transgenic Animals" in Roitt (ed.) *Encyclopedia of Immunology*, Academic Press, pp. 1502–1504, 1992.
James, Stephen P., "Cellular Immune Mechanisms in the Pathogenesis of Crohn's Disease," *In vivo*, vol. 2, pp. 1–8, 1988.
Jewell, D. P., *Oxford Textbook of Medicine*, Oxford University of Press, "Crohn's Disease," pp. 12.121–12.132.
Travis, John, "Scoring a Technical Knockout in Mice," *Science*, vol. 256, pp. 1392–1394, Jun. 5, 1992.
Kirsmer, "Inflammatory Bowel Disease", *Disease Monitor*, vol. 37, pp. 610–666, 1991.
Pullman, et al., "Enhanced Mucosal Cytokine Production in Inflammatory Bowel Disease," *Gastroenterology*, vol. 102, pp. 529–537, 1992.
Reinecker, et al., "Proinflammatory Cytokines in Intestinal Mucosa," *Immunol Res.* vol. 10, pp. 247–248, 1991.
Sawyerr, et al., "Review Article: the Pharmacological Implications of Leucocyte–Endothelial Cell Interactions in Crohn's Disease," *Aliment. Pharmacol. Therap.*, vol. 5, pp. 1–14, 1991.
Schreiber, et al., "Die Rolle des Arachidonsaure–Stoffwechsels in der Pathophysiologie chronisch–entzundlicher Darmerkrankungen. Eicosanoids in Inflammatory Bowel Diseases," *Immun. Infekt.*, vol. 18, pp. 115–120, Apr., 1990, (Abstract in English).
"Chronic Inflammation Diseases of the Bowel," Berkow (ed.), Merck Manual, Merck & Co., Rahway, New Jersey, pp. 797–806.

*Primary Examiner*—Michael G. Wityshyn
*Assistant Examiner*—C. Sayala
*Attorney, Agent, or Firm*—Edwin P. Ching; Karen B. Dow; Lauren C. O'Neal

[57] ABSTRACT

The invention provides in vivo methods and compositions for using IL-10 to treat inflammatory bowel disease in a mammal. The method comprises administering to the mammal an effective amount of IL-10, preferably intravascularly, alone or in combination with other therapeutic reagents.

25 Claims, No Drawings

USE OF IL-10 TO TREAT INFLAMMATORY BOWEL DISEASE

BACKGROUND OF THE INVENTION

The invention relates generally to manipulation of the human immune response to ameliorate or alter signs or symptoms of inflammatory conditions or diseases relating to inflammation, immunity, or autoimmunity. More specifically, the invention relates to treatment of inflammatory bowel disease using interleukin-10 (IL-10).

The immune system is diverse and complex. It includes a multitude of natural and adaptive immune mechanisms and reactions. For practical purposes, the immune system is often thought of in terms of either humoral and cellular immune responses. Humoral immunity refers broadly to antibody production and actions by B-cells including plasma cells. Cellular immunity is mediated by cells including T-cells, monocytes, macrophages and histiocytes. T-cells and B-cells are two broad categories of lymphocytes. T-cells may be further categorized according to their various functions or markers. For instance, T-cells can be classified as T helper cells or T suppressor cells. Additionally, T-cells can be activated to become cytotoxic or to perform other more specialized functions. Normally, T-cells and B-cells have interactions that may regulate each other's activity to some extent. See, e.g., Paul (ed.) *Fundamentals of Immunology* (2d ed.) Raven Press, New York (1989).

For instance, for different antigens either cellular or humoral responses may predominate, typically, in a mutually exclusive fashion. The severity of some diseases, e.g., leprosy, leishmaniasis, and some types of autoimmunity, may be due the inappropriate dominance of one class of response over the other. Mosmann et al., *Immunol. Today* 8:223–227 (1987); Mosmann et al., *Ann. Rev. Immunol.* 7:145–173 (1989); Parish, *Transplant. Rev* 13:35–66 (1972); and Liew, *Immunol. Today* 10:40–45 (1989).

One of the mechanisms by which the immune system normally regulates itself includes the production of proteins called cytokines. For example, lymphokines are cytokines produced by T-cells and some B-cells, and monokines are cytokines produced by monocytes. Cytokines, which may be glycosylated, mediate numerous immune responses.

IL-10 is a cytokine capable of mediating a number of actions or effects. IL-10 has been isolated from both mouse and human cells and is involved in controlling the immune responses of different classes or subsets of T helper (Th) cells. Th cells can be divided into different subsets that are distinguished by their cytokine production profiles. Th1 T cell clones produce interleukin-2 (IL-2) and interferon-$\gamma$ (IFN-$\gamma$) whereas Th2 cell clones secrete IL-10, IL-4, and IL-5, generally following activation by antigens or mitogenic lectins. Both classes of Th cell clones produce cytokines such as tumor necrosis factor-$\alpha$ (TNF-$\alpha$), IL-3, and granulocyte-macrophage colony stimulating factor (GM-CSF). A third category of Th cells (Th0) produces IL-2, IFN-$\gamma$, IL-4, IL-5, TNF-$\alpha$, IL-3, and GM-CSF simultaneously.

The different cytokine production patterns of Th1 and Th2 cells reflect their helper functions. Th1 cells are predominantly involved in delayed-type hypersensitivity (DTH) responses, whereas Th2 cells are associated with antibody production. Since antibody (Th2 pathways) and DTH (Th1 pathways) responses are often mutually exclusive, Th1 and Th2 cells are thought to have cross-regulatory effects. IFN-$\gamma$ produced by Th1 cells inhibits proliferation of Th2 cells, and IL-10 produced by Th2 cells inhibits cytokine synthesis by Th1 cell clones, especially IFN-$\gamma$ and IL-2 production.

DTH is an example of a cell-mediated immune response. DTH is characterized by edema and cellular infiltration of the tissue, generally by T cells and monocytes and/or macrophages. Some sets of cytokines are separately associated with DTH reactions and humoral immune responses. Cher et al., *J. Immunol.* 138:3688–3694 (1987); and Mosmann et al. (1987 and 1989). Diseases associated with these classes of response may be caused by inappropriate production of associated sets of cytokines.

As an example of inappropriate cytokine production, evidence suggests that excessive production of IFN-$\gamma$ is responsible for major histocompatibility complex (MHC) associated autoimmune diseases. Treatment of such diseases can include manipulation of selected cytokines. See generally International Application No. PCT/US 90/03554, Publication No. WO 9100349, which discloses compositions and use of IL-10 for treatment of diseases relating to imbalanced or inappropriate immune response, and which is incorporated by reference herein.

Because inflammatory responses are often mediated by cytokine activity, agents that could manipulate synthesis of cytokines would be advantageous for therapy of selected diseases. The present invention relates generally to manipulation of cytokine synthesis and specifically to using IL-10 to treat inflammatory bowel diseases such as ulcerative colitis and Crohn's Disease.

Inflammatory bowel disease (IBD) refers to a group of gastrointestinal disorders characterized by a chronic non-specific inflammation of portions of the gastrointestinal tract. Ulcerative colitis and Crohn's Disease are the most prominent examples of IBD in humans. They are associated with many symptoms and complications, including growth retardation in children, rectal prolapse, blood in stools (e.g., melena and/or hematochezia), wasting, iron deficiency, and anemia, e.g. iron deficiency anemia and anemia of chronic disease or of chronic inflammation. The etiology or etiologies of IBD are unclear. See, Wyngaarden and Smith (eds.) *Cecil's Textbook of Medicine* (W.B. Saunders Co. 1985), Berkow (ed.) *The Merck Manual of Diagnosis and Therapy* (Merck Sharp & Dohme Research Laboratories, 1982), and *Harrison's Principles of Internal Medicine*, 12th Ed., McGraw-Hill, Inc. (1991), all of which are incorporated herein by reference.

Ulcerative colitis refers to a chronic, non-specific, inflammatory, and ulcerative disease having manifestations primarily in the colonic mucosa. It is frequently characterized by bloody diarrhea, abdominal cramps, blood and mucus in the stools, malaise, fever, anemia, anorexia, weight loss, leukocytosis, hypoalbuminemia, and an elevated erythrocyte sedimentation rate (ESR). Complications can include hemorrhage, toxic colitis, toxic megacolon, occasional rectovaginal fistulas, and an increased risk for the development of colon cancer.

Ulcerative colitis is also associated with complications distant from the colon, such as arthritis, ankylosing spondylitis, sacroileitis, posterior uveitis, erythema nodosum, pyoderma gangrenosum, and episcleritis. Treatment varies considerably with the severity and duration of the disease. For instance, fluid therapy to prevent dehydration and electrolyte imbalance is frequently indicated in a severe attack. Additionally, special dietary measures are sometimes useful. Medications include various corticosteroids, sulphasalazine and some of its derivatives, and possibly immunosuppressive drugs.

Crohn's Disease shares many features in common with ulcerative colitis. Crohn's Disease is distinguishable in that lesions tend to be sharply demarcated from adjacent normal bowel, in contrast to the lesions of ulcerative colitis which are fairly diffuse. Additionally, Crohn's Disease predominately afflicts the ileum (ileitis) and the ileum and colon (ileocolitis). In some cases, the colon alone is diseased (granulomatous colitis) and sometimes the entire small bowel is involved (jejunoileitis). In rare cases, the stomach, duodenum, or esophagus are involved. Lesions include a sarcoid-type epithelioid granuloma in roughly half of the clinical cases. Lesions of Crohn's Disease can be transmural including deep ulceration, edema, and fibrosis, which can lead to obstruction and fistula formation as well as abscess formation. This contrasts with ulcerative colitis which usually yields much shallower lesions, although occasionally the complications of fibrosis, obstruction, fistula formation, and abscesses are seen in ulcerative colitis as well.

Treatment is similar for both diseases and includes steroids, sulphasalazine and its derivatives, and immunosuppressive drugs such as cyclosporin A, mercaptopurine and azathioprine.

The severe complications of IBD can be seriously debilitating, and eventually may lead to death. Thus, a need exists for effective treatment, both prophylactic and curative, to alleviate the symptoms. The present invention provides both.

SUMMARY OF THE INVENTION

The invention provides methods of treating an IBD in a mammal comprising administering to the mammal an effective amount of IL-10. IBD includes ulcerative colitis and Crohn's Disease. The administration is preferably parenteral, such as intravascular. Most preferably, the administration is intravenous and the mammal treated is a human.

The effective amount of IL-10 is selected from a range of about 1 microgram to about 100 milligrams per kilogram of body weight. More preferably, the effective amount is selected from a range of about 10 micrograms to about 1000 micrograms per kilogram of body weight. Most preferably, the effective amount is selected from a range of about 50 micrograms to about 100 micrograms per kilogram of body weight.

IL-10 can be administered alone or in combination with at least one additional therapeutic agent. Examples of such agents include corticosteroids, sulphasalazine, derivatives of sulphasalazine, immunosuppresive drugs such as cyclosporin A, mercaptopurine, and azathioprine, and another cytokine. The co-administration can be sequential or simultaneous. Co-administration generally means that the multiple (two or more) therapeutics are present in the recipient during a specified time interval. Typically, if a second agent is administered within the half-life of the first agent, the two agents are considered co-administered.

The invention further provides a method of predicting a mammal's predisposition for development of an inflammatory condition characterized by suboptimal levels of IL-10 comprising assaying a sample taken from the mammal for an IL-10 level. Suboptimal levels include undetectable amounts. A detectable level could be compared to a known normal level of IL-10. Alternatively, one can assay for inflammatory mediators such as IL-1, IL-6, TNF, and IFN-$\gamma$ by using commercially available kits. Overproduction of one of these mediators can indicate that insufficient amounts of IL-10 are available. Preferably, blood is the sample source. The method allows for prediction of predisposition to a number of inflammatory conditions, such as an IBD or an anemia, an arthritis, a dermatitis, or other syndrome associated with an IBD. The IBD is usually ulcerative colitis or Crohn's Disease.

Pharmaceutical compositions are also provided. A composition for administration to a mammal having an IBD, such as ulcerative colitis or Crohn's Disease, includes an amount of IL-10 effective to ameliorate at least one of a symptom or a sign of the IBD in the mammal and a pharmaceutically acceptable additive. Typically, the mammal is a human. The effective amount of IL-10 is selected from a range of about 1 microgram to about 100 milligrams per kilogram of body weight of the mammal. More preferably, the effective amount is selected from a range of about 10 micrograms to about 1000 micrograms per kilogram of body weight. Most preferably, the effective amount is selected from a range of about 50 micrograms to about 100 micrograms per kilogram of body weight.

Generally, the term "symptoms" refers any subjective evidence of disease or of a patient's condition. This includes evidence as percieved by the patient. Examples of symptoms of IBD include diarrhea, abdominal pain, fever, melena, hematochezia, and weight loss. The term "signs" refers generally to any objective evidence of a disease or condition, usually as percieved by an examining physician or features which would reveal themselves on a laboratory evaluation or other tests such as an ultrasonic study or a radiographic test. Some examples of signs of IBD include abdominal mass, glossitis, aphthous ulcer, anal fissure, perianal fistula, anemia, malabsorption, and iron deficiency. Occasionally, signs and symptoms overlap. For example, the patient complains of bloody stools (a symptom), and a laboratory test of a stool sample is positive for blood (a sign).

Pharmaceutical compositions of the invention are preferably in a form suitable for parenteral administration. Preferably, the effective amount is a unit dose presented in an ampoule. Alternatively, the effective amount could be presented in a vial containing multiple doses or it could be offered in some other form. Examples of pharmaceutically acceptable additives include vehicles such as aqueous vehicles, buffers, diluents, antimicrobials, and preservatives.

DESCRIPTION OF THE PREFERRED EMBODIMENT

Because IL-10 inhibits cytokine production, the invention can be useful to control an immune response relating to cytokine production. The present invention establishes that IBD is related to the absence of IL-10. More specifically, the invention provides methods of treating IBD using IL-10.

A Murine Model for IBD

A murine model of IBD has been developed. This model contributes to elucidation of the etiology or mechanism of IBD. Additionally, it provides an experimental forum for various therapeutic agents. To develop the model, the IL-10 gene is either removed or rendered ineffective or non-expressible in the experimental animal. The animal is referred to as having the IL-10 gene "knocked out" or as being a "knockout" (KO) animal. The KO can be accomplished by any of several means known in the art. For example, a transgenic animal whose IL-10 gene has been inactivated could be produced. See Goodnow, C., "Transgenic Animals," 1502–1504, *Encyclopedia of Immunology*, Roitt (ed.), Academic Press, San Diego (1992). Briefly, purified DNA is microinjected into the pronuclei of fertilized oocytes. Afterwards, the oocytes are surgically implanted into the oviducts of foster mothers. Alternatively, standard genetic breeding techniques may be used to isolate a homozygous mutant animal strain.

Additionally, there are methods which inactivate specific genes in the germ line of mice. In this case, a mutant transgene is introduced in place of the wild-type gene through homologous recombination. Embryonal stem (ES) cell lines "can be isolated and culture in vitro from mouse blastocysts, and later reimplanted into another blastocyst so as to partly colonize both the somatic and germ-line tissues of the resulting mouse." Goodnow at 1503. DNA is introduced in the ES cells in culture and the blastocysts are surgically implanted in a foster mother. Heterozygous mutant progeny result which are mated to each other so that, ultimately, offspring having two mutant alleles, e.g., a homozygous mutant, are produced. These offspring would have no functional alleles of the gene of interest and allow for "genetic dissection" to remove specific genes. Analysis of the resulting offspring can provide insight into the role of the targeted gene in the KO mice in causing resultant phenotypes.

For additional methods of creating an experimental animal having deletion of a particular gene, see McMahon, et al., "The Midbrain-Hindbrain Phenotype of $Wnt$-$1^-$/$Wnt$-$1^-$ Mice Results from Stepwise Depletion of $engrailed$-Expressing Cells by 9.5 Days Postcoitum," *Cell* 69:581–595 (May 15, 1992) and Travis, "Scoring a Technical Knockout in Mice," *Science* 256:1392–1394 (Jun. 5, 1992). Additional applicable technologies include the art of mutagenesis and antisense technologies. See Goodnow, C. (1992).

Sources of IL-10

IL-10 suitable for use in the invention can be obtained from a number of sources. For example, it can be isolated from culture media of activated T-cells capable of secreting the protein. Additionally, the polypeptide or active fragments thereof can be chemically synthesized using standard techniques as known in the art. See, e.g., Merrifield *Science* 233:341–47 (1986) and Atherton et al. *Solid Phase Peptide Synthesis, A Practical Approach*, I.R.L. Press, Oxford (1989), which are incorporated herein by reference.

Preferably, the protein or polypeptide is obtained by recombinant techniques using isolated nucleic acids encoding for the IL-10 polypeptide. General methods of molecular biology and described, e.g., in Sambrook, et al., *Molecular Cloning, A Laboratory Manual*, Cold Spring Harbor Publish., Cold Spring Harbor, N.Y., 2d ed. 1989 and Ausubel et al. (eds.) *Current Protocols in Molecular Biology*, Green/Wiley, New York (1987 and periodic supplements), which are incorporated herein by reference. The appropriate sequences can be obtained using standard techniques from either genomic or cDNA libraries. Libraries are constructed from nucleic acid extracted from the appropriate cells. See, for example, International Application No. PCT/US 90/03554, Publication No. WO 9100349, incorporated by reference herein, which discloses recombinant methods to make IL-10. Useful gene sequences can be found, e.g., in various sequence databases, e.g., Gen Bank and EMBL for nucleic acid, and PIR and Swiss-Prot for protein, c/o Intelligenetics, Mountain View, Calif.; or the Genetics Computer Group, University of Wisconsin Biotechnology Center, Madison, Wis., which are incorporated herein by reference.

Clones comprising sequences that encode human-IL-10 have been deposited with the American Type Culture Collection (ATCC), Rockville, Md. under the Accession Numbers 68191 and 68192. Identification of clones harboring the sequences encoding IL-10 is performed by either nucleic acid hybridization or immunological detection of the encoded protein, if an expression vector is used. Oligonucleotide probes based on the deposited sequences disclosed in International Application No. PCT/US 90/03554, Publication No. WO 9100349 are particularly useful. Oligonucleotide probes useful for identification of the sequences can also be prepared from conserved regions of related genes in other species. Alternatively, degenerate probes based on the amino acid sequence of IL-10 can be used.

Standard transfection methods can be used to produce prokaryotic, mammalian, yeast or insect cell lines which express large quantities of the polypeptide. Exemplary *E. coli* strains suitable for both expression and cloning include W3110 (ATCC No. 27325), JA221, C600, ED767, DH1, LE392, HB101, X1776 (ATCC No. 31244), X2282, RR1 (ATCC No. 31343). Exemplary mammalian cell lines include COS-7 cells, mouse L cells and CHO cells. See Sambrook (1989) and Ausubel et al. (1987 and supplements).

Various expression vectors can be used to express the gene. Conventional vectors used for expression of recombinant proteins in prokaryotic or eukaryotic cells may be used. Preferred vectors include the pcD vectors described in Okayama et al. *Mol. Cell. Biol.* 3:280–289 (1983); and Takebe et al., *Mol. Cell. Biol.* 466–472 (1988), which are incorporated herein by reference. Other SV40-based mammalian expression vectors include those disclosed in Kaufman et al., *Mol. Cell. Biol.* 2:1304–1319 (1982) and U.S. Pat. No. 4,675,285, both of which are incorporated herein by reference. These SV40-based vectors are particularly useful in COS7 monkey cells (ATCC No. CRL 1651), as well as other mammalian cells such as mouse L cells. See also, Pouwels et al. (1989 and supplements) *Cloning Vectors: A Laboratory Manual*, Elsevier, N.Y.

Peptides of the invention may be expressed in soluble form such as a secreted product of a transformed yeast or mammalian cell. In this situation, the peptide can be purified according to standard procedures well known in the art. For example, purification steps could include ammonium sulfate precipitation, ion exchange chromatography, gel filtration, electrophoresis, affinity chromatography, and the like. See Jakoby (ed.), "Enzyme Purification and Related Techniques," *Methods in Enzymology* 22:233–577 (1977); Scopes, R., *Protein Purification Principles and Practice* (Springer-Verlag, New York, 1982); and Deutscher (ed.) "Guide to Protein Purification," *Methods in Enzymology*: 182, Academic Press, New York (1990); all three references are incorporated herein by reference.

Alternatively, IL-10 may be expressed in insoluble form such as aggregates or inclusion bodies. These peptides are purified as described herein, or by standard procedures known in the art. Examples of purification steps include separating the inclusion bodies from disrupted host cells by centrifugation, solubilizing the inclusion bodies with chaotropic agents and reducing agents, diluting the solubilized mixture, and lowering the concentration of chaotropic agent and reducing agent so that the peptide assumes a biologically active conformation. For specifics of these procedures, see the following references: Winkler, et al., *Biochemistry* 25:4041–4045 (1986); Winkler, et al., *Biotechnology* 3:992–998 (1985); Koths, et al. U.S. Pat. No. 4,569,790; all of which are incorporated by reference herein.

The nucleotide sequences used to transfect the host cells can be modified according to standard techniques to yield IL-10 polypeptides or fragments thereof, with a variety of desired properties. IL-10 polypeptides can be readily designed and manufactured utilizing various recombinant DNA techniques, including these well known to those skilled in the art. The modified polypeptides can vary from the naturally-occurring sequence at the primary structure level by amino acid, insertions, substitutions, deletions, fusions, and the like. These modifications can be used in a number of combinations to produce the final modified protein chain.

The amino acid sequence variants can be prepared with various objectives in mind, including increasing serum half life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylation variants or proteins which are conjugated to polyethylene glycol (PEG), etc. The variants typically exhibit some of the same biological activities as naturally occurring IL-10. However, the variants that are not capable of binding the IL-10 receptor on the appropriate target cell are useful nonetheless (a) as a reagent in diagnostic assays for IL-10, (b) as agents for purifying antibodies from antisera or hybridoma culture supernatants when insolubilized in accord with known methods, and (c) as immunogens for raising antibodies to IL-10, so long as at least one IL-10 epitope remains active.

In general, modifications of the sequences encoding the polypeptides may be readily accomplished by a variety of techniques, such as site-directed mutagenesis (see, Gillman and Smith, *Gene* 8:81–97 (1979) and Roberts, S. et al., *Nature* 328:731–734 (1987), both of which are incorporated herein by reference). Most modifications are evaluated by routine screening in a suitable assay for the desired characteristic. For instance, International Application No. PCT/US 90/03554, Publication No. WO 9100349, describes a number of in vitro assays suitable for identifying IL-10 activity.

Preferably, human IL-10 is produced and purified for use in the invention. Additionally, murine IL-10 (mIL-10) can be used. Production and purification of mIL-10 is as follows. mIL-10 is produced in *E. coli* as inclusion bodies which are isolated by lysing the E. coli cell and centrifuging the resultant supernatant at about 13,000 g. The resultant pellet is collected and washed by homogenizing in an appropriate buffer to remove contaminant proteins.

The inclusion bodies are solubilized in a suitable buffer containing 6 molar (M) guanidine hydrochloric acid (HCl) and 10 millimolar (mM) dithiothreitol (DTT) in the proportion of 10 ml buffer per gram of inclusion bodies. The mixture is incubated at 4° C. for 3 hours. After 3 hours, the solubilized inclusion bodies are diluted 100 fold with buffer containing 0.5M guanidine HCl, reduced glutathione, and oxidized glutathione in a ratio of 2:1 and protease inhibitors at pH 8.5, and allowed to refold for 18 hours at 4° C. in the presence of a nitrogen atmosphere. The refolded material is filtered and solid diammonium sulfate [$(NH_4)_2SO_4$] is added to make the final concentration 25%.

The material is loaded onto a hydrophilic interaction column using phenyl sepharose, butyl sepharose or toyo pearl. The column is washed with 10 bed volumes of 25% $(NH_4)_2SO_4$ in buffer (TRIS 30 mM, $(NH_4)_2SO_4$ at 25% saturation, and tetra sodium EDTA 10 mM at pH 8.5) and eluted with a buffer containing no diammonium sulfate (TRIS 30 mM, NaCl 30 mM, and tetra sodium EDTA 10 mM at pH 8.5).

The eluate peak fractions are collected, assayed, analysed and pooled. The pools are adjusted to pH 9.0 and conductivity 5.0 mhos. The pools are loaded onto a Q Sepharose column and the flow is collected. This flow-through contains the active fraction of mIL-10. The material that is bound to the column contains inactive mIL-10 and is eluted with 1.0M sodium chloride (NaCl).

The active fractions are pooled, analysed, assayed and adjusted to pH 7.0 and conductivity 5.0–6.0 mhos. The material is loaded onto an S-Sepharose column. The flow-through fractions are collected. The column is washed with 10 bed volumes of 20M HEPES (N-[2-hydroxyethyl]piperazine-N-[2-ethanesulfonic acid]) pH 7.0, which is the equilibration buffer. The column is eluted with a NaCl gradient from 0–6M. The peak fractions are pooled and analysed, and contain active, 95% pure, mIL-10. The purified mIL-10 is stored at 4° C. under sterile aseptic conditions. The final product has pyrogen levels of less than 0.1 endotoxin units (EU)/ml.

In addition to obtention by recombinant techniques, peptides such as IL-10 or active fragments thereof can be synthesized in solid or liquid phase as is known in the art. Peptides can be synthesized at different substitution levels and the synthesis may follow a stepwise format or a coupling approach. The stepwise method includes condensing amino acids to the terminal amino group sequentially and individually. The coupling, or segment condensation, approach involves coupling fragments divided into several groups to the terminal amino acid. Synthetic methods include azide, chloride, acid anhydride, mixed anhydride, active ester, Woodward reagent K, and carbodiimidazole processes as well as oxidation-reduction and other processes. These processes apply to both solid and liquid phase synthesis. See Merrifield (1988) and Atherton et al. (1989).

The synthetic peptides are usually purified by a method such as gel filtration chromatography or high performance liquid chromatography. See, for example, Stewart & Young, *Solid Phase Peptide Synthesis,* Pierce Chemical Company, Rockford, Ill. (1984), Villafranca (ed.) (1991) *Techniques in Protein Chemistry II,* Academic Press, New York, and other publications from The Protein Society described therein, and which are incorporated by reference herein.

Treatment of IBD

A method for treating IBD is provided. Briefly, IL-10 is administered, e.g., intravascularly, in an effective amount to a mammal having IBD.

When referring to IL-10, active fragments thereof, analogs and homologs are included. Active fragments, analogs and homologs to IL-10 include those proteins, polypeptides, or peptides which possess one or more various characteristic IL-10 activities. Any of these proteinaceous entities can be glycosylated or unglycosylated. Examples of IL-10 activity include inhibition or substantial reduction of the level of production of at least one of the following cytokines: IFN-$\gamma$, Interleukin-2 (IL-2), lymphotoxin, Interleukin-3 (IL-3), or granulocyte-macrophage colony stimulating factor (GM-CSF). IL-10 activity also includes inhibition of cytokine production by activated macrophages, e.g., IL-1, IL-6, TNF$\alpha$, which are potent inflammatory mediators. These activated macrophages likely mediate the severe inflammatory effects observed in IBD.

For examples of procedures and assays to determine IL-10 activity, see Publication No. WO 9100349 which is incorporated by reference herein. This patent application also provides proteins having IL-10 activity and production of such proteins including recombinant and synthetic techniques.

Additionally, biological assays of the cytokines themselves can also be used to determine IL-10 activity. A biological assay for human lymphotoxin is disclosed in Aggarwal, *Methods in Enzymology* 116; 441-447 (1985) and Matthews, et al., (Clemens, et al., eds.), *Cytokines and Interferons; A Practical Approach:* 221-225 (IRL Press, Washington, D.C. 1987). These are hereby incorporated by reference. Human IL-2 and GN-CSF can be assayed with factor dependent cell lines CTLL-2 and KG-1, available from the ATCC under accession numbers TIB 214 and CCL 246, respectively. Human IL-3 can be assayed by its ability to stimulate the formation of a wide range of hematopoietic cell colonies in soft agar cultures, e.g., as described by Metclaf, "The Hemopoietic Colony Stimulating Factors" (Elsevier, Amsterdam, 1984). IFN-$\gamma$ can be quantified with anti-viral assays, e.g., Meager in Clemens, et al. (eds.) at 129-147. Monitoring of these cytokines can provide useful information on when an effective amount of IL-10 has been reached.

Pharmaceutical Compositions

To prepare pharmaceutical compositions including the polypeptide IL-10, the polypeptide is admixed with a pharmaceutically acceptable carrier or excipient which is preferably inert. Preparation of such pharmaceutical compositions is known in the art; see, for example, *Remington's Pharmaceutical Sciences* and *U.S. Pharmacopeia: National Formulary*, Mack Publishing Company, Easton, Pa. (1984).

The polypeptide may be administered in aqueous vehicles such as water, saline or buffered vehicles with or without various additives and/or diluting agents. Alternatively, a suspension, such as a zinc suspension, can be prepared to include the peptide. Such a suspension can be useful for subcutaneous (SQ) or intramuscular (IM) injection.

The proportion of peptide and additive can be varied over a broad range so long as both are present in effective amounts. On a per-dose basis, the amount of the peptide could range from about 1 microgram ($\mu$g) to about 100 milligrams (mg).

The total daily dose ranges from about 1 microgram to about 100 milligrams per kilogram of body weight. More preferably, the dose is selected from a range of about 10 micrograms to about 1000 micrograms per kilogram of body weight. Most preferably, the dose is selected from a range of about 50 micrograms to about 100 micrograms per kilogram of body weight. Dosages are on a schedule which effects the desired treatment and can be periodic over short or longer term.

Compositions may be ingested orally or injected into the body. Formulations for oral use include compounds to protect the polypeptides from proteases which occur in the gastrointestinal tract. Injections are usually intramuscuiar, subcutaneous, intradermal or intravenous. Alternatively, intra-articular injection or other routes could be used in appropriate circumstances. Additionally, compositions including the peptide IL-10 may be implanted into a patient or injected using a drug delivery system. See, for example, Urquhart, et al., *Ann. Rev. Pharmacol. Toxicol.* 24:199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Preferably, the peptide is administered parenterally and preferably in a unit dosage injectable form. Examples of an injectable form include solutions, suspensions and emulsions. More preferably, an effective amount of IL-10 is administered intravenously.

The phrase "effective amount" means an amount sufficient to ameliorate a symptom or sign of an autoimmune condition or of an undesirable or inappropriate inflammatory or immune response. Typical mammalian hosts will include mice, rats, cats, dogs, and primates, including humans. An effective amount for a particular patient may vary depending on factors such as the condition being treated, the overall health of the patient, the method route and dose of administration and the severity of side affects.

Determination of the appropriate dose is made by the clinician using parameters known in the art. Generally, the dose begins with an amount somewhat less than the optimum dose and it is increased by small increments thereafter until the desired or optimum effect is achieved. See generally *The Merck Manual* § 269 ,"Pharmacokinetics and Drug Administration." TNF$\alpha$, IFN-$\gamma$, IL-1, and IL-6 levels would be important indicators of when an effective dose is reached. Preferably, an IL-10 molecule derived from the species of the treatment target animal will be used.

Typically, the peptide is injected in association with a pharmaceutical carrier such as normal saline, Ringer's solution, dextrose solution, and other aqueous carriers known in the art. Appropriate non-aqueous carriers may also be used and examples include fixed oils and ethyl oleate. A preferred carrier is 5% dextrose in saline. Frequently, it is desirable to include additives in the carrier such as buffers and preservatives or other substances to enhance isotonicity and chemical stability.

The total daily dose may be given as a single injection, a continuous infusion, or it may be divided into several smaller doses for bolus intravenous administration or administration by some other route such as intramuscular injection. Preferably, the IL-10 is administered as an intravenous bolus. IL-10 may be administered alone or in combination with other therapeutic agents. Examples of such agents include corticosteroids, sulphasalazine, derivatives of sulphasalazine, and selected cytotoxic drugs such as cyclosporin A, mercaptopurine, and azathioprine. Typically, the multiple medications are separately infused or injected sequentially. In appropriate circumstances, multiple medications are mixed and infused or injected simultaneously together, e.g., IL-10 with other cytokines, steroids, or other therapeutic reagents.

It should be noted that IBD symptoms may be episodic, so effective treatment may be achieved by administration of small doses at opportune moments. Alternatively, small amounts of continuous administration may provide long periods of episode-free health for suffering target animals.

The following examples are provided by way of illustration and not by way of limitation. Those of skill will readily recognize non-critical parameters which can be varied to accomplish the invention described herein.

EXAMPLES

1. Murine Model for Inflammatory Bowel Disease

Mice which were devoid of the IL-10 gene were raised. See Kuhn et al. *Science* 254:707-710 (1991); Capecchi, *Science* 244:1288 (1989); Robertson (ed.) *Teratocarcinomas and embryonic stem cells: A Practical Approach*, I.R.L. Press, Oxford (1987); and Zijestra, et al. *Nature* 336:348-352 (1989), for descriptions of the general technology and for the procedures to make mice devoid of a selected gene. These references are all incorporated herein by reference. In the following examples, mice which lack the IL-10 gene are referred to as IL-10T mice or knock out (KO) mice.

First Group. Four mice were sacrificed for bone marrow assays. A portion of their marrow was analyzed to determine their ability to produce myeloid and erythroid progenitors [see table W] and to assess production of stem cells [see table X]. A remaining portion of the marrow was used for long-term bone marrow cultures to assess the capability of micro-environmental cells to support normal hematopoietic generation. The thymus and spleen contained normal numbers of T-cells and normal numbers of B-cells. The short-term progenitor and stem-cell assays are given in tabular form below. The cells from the controls and the knock-out mice were separately pooled.

TABLE W

| NUMBER OF COLONY-FORMING CELLS/FEMUR | | | | | | |
|---|---|---|---|---|---|---|
| | Total cells/femur | GM | BFU-e | CFU-e | Meg | Meg/Mix |
| Control | 9.5 × 10⁶ | 18,430 | 475 | 42,500 | 2,470 | 285 |
| IL-10T | 9.4 × 10⁶ | 21,902 | 940 | 59,740 | 2,271 | 658 |

GM = granulocytes and macrophages; BFU = blood forming units; CFU = colony forming units; -e = erythroid; Meg = megakaryocyte colonies; Meg/Mix = megakaryocytes mixed with other lineages. Colony-stimulating factors used in assay: IL-3 + IL-6 + erythropoietin (Epo)

TABLE X

| NUMBERS OF DAY-14 CFU-S | |
|---|---|
| Control group | 1,678 per femur |
| IL-10T group | 1,517 per femur |

Stem cell production is the number of CFU-S in a femur of the mouse. CFUS measures the formation of hemopoietic nodules in the spleen of lethally irradiated mice following transplantation. See Till et al. (1961) *Radiation Research* 14:213.

Conclusion. The IL-10T mice did not show any obvious defect in the production of myeloid, erythroid and stem cells. Concurrently, the long-term cultures had formed a layer of supportive stroma in all cultures including those from IL-10T mice. These cultures are set up in two stages: First, cells are put into culture to form the complex stromal layers needed to support continuous hematopoiesis. Then the cultures are reseeded with additional bone marrow cells from equivalent types of donors to provide the actual precursors that associate with the stromal cells. This second stage was undertaken when the second and third groups of mice were available.

Second and third groups. The bone marrow cells from these animals were needed to complete the long-term bone marrow culture experiments. In addition to using their bone marrow for this purpose, other procedures were done. The IL-10T animals were anemic but seemed to have normal levels of bone marrow precursors. Therefore, their anemia was evaluated and their organs were observed histologically.

| | PERIPHERAL BLOOD COUNTS | | |
|---|---|---|---|
| MICE | WBC/mL × 10⁶ | RBC/mL × 10⁹ | Platelets/mL × 10⁸ |
| Control | | | |
| #1 | 7.2 | 7.3 | 12.6 |
| #2 | 11.2 | 5.6 | 10.7 |
| #3 | 10.0 | 6.7 | 8.5 |
| #4 | 8.2 | 5.6 | 9.8 |
| #5 | 7.7 | 5.6 | 8.0 |
| IL-10T | | | |
| #1 | 4.0 | 2.4 | 20.6 |
| #2 | 4.8 | 7.1 | 8.0 |
| #3 | 7.5 | 3.9 | 27.3 |
| #4 | 6.5 | 5.5 | 23.9 |

WBC = white blood cells, RBC = red blood cells

| | PERIPHERAL BLOOD DIFFERENTIAL | | | | |
|---|---|---|---|---|---|
| MICE | % Lymphs | % Neut | % Mono | % Eos | % Retics |
| Control | | | | | |
| #1 | 87 | 12 | 1 | 0 | 2.4 |
| #2 | 72 | 26 | 2 | 0 | 1.2 |
| #3 | 80 | 18 | 1 | 1 | 0.6 |
| IL-10T | | | | | |
| #1 | 36 | 64 | 0 | 1 | 3.8 |
| #2 | 40 | 57 | 0 | 3 | 5.3 |
| #3 | 23 | 77 | 0 | 0 | 17.1 |

Lymphs = lymphocytes, Neut = neutrophils, Mono = monocytes, Eos = eosinophils, Retics = reticulocytes RBC Morphology. All control animals had normal appearing red blood cells (RBC's). The IL-10T mice showed variable morphologies. IL-10T #1 had microcytic cells; #2 and #3 had microcytic cells plus some macrocytic, polychromic cells and occasional nucleated red blood cells (NRBC's). Red blood smears were stained with new methylene blue and the cells showing ribosomal staining were enumerated. Positive staining occurs in very young red blood cells, reticulocytes, and implies premature release from hemopoietic organs. This is referred to as the reticulocyte count.

Organ Histology of IL-10T Mice. Inspection of sectioned heart, lung, kidney, and thymus appeared normal. The liver appeared normal except for occasional foci of mononuclear and neutrophilic granulocytes. The spleens were grossly abnormal. Follicles were present but the red pulp area was filled with hematopoietic cells, mostly NRBC's and blast forms (immature cells).

There were few or no mature RBC's and there was no iron storage with the macrophages.

SPLEEN CELL DIFFERENTIAL

| CE | cells/ spleen | (% of total cells) | | | | | | |
|---|---|---|---|---|---|---|---|---|
| | | Lymph | Mono | Neu | Eos | Plasma cell | Blast | Nuc RBC |
| Control | | | | | | | | |
| #1 | $1.5 \times 10^8$ | 88 | 2 | 1 | <1 | <1 | 1 | 6 |
| #2 | $1.5 \times 10^8$ | 89 | 1 | <1 | <1 | <1 | 2 | 7 |
| #3 | $1.1 \times 10^8$ | 79 | 3 | 4 | 1 | 2 | 2 | 8 |
| IL-10T | | | | | | | | |
| #1 | $2.1 \times 10^8$ | 64 | 2 | 7 | 1 | 1 | 2 | 22 |
| #2 | $2.5 \times 10^8$ | 54 | 2 | 13 | 3 | 1 | 6 | 21 |
| #3 | $1.6 \times 10^8$ | 43 | 2 | 10 | 1 | 1 | 10 | 32 |

Lymph = lymphocytes, Mono = monocytes, Neu = neutrophils, Eos = eosinophils, Retics = reticulocytes, Blast = blastocyte, Nuc RBC = nucleated red blood cell

BONE MARROW DIFFERENTIALS (% of Total)

| MICE | Neu | Neu MB | Eos | Eos MB | Nuc RBC | Plasma cell | Lymph | Blast Undif. |
|---|---|---|---|---|---|---|---|---|
| Control | | | | | | | | |
| #1 | 46 | 12 | 10 | 4 | 20 | 1 | 4 | 4 |
| #2 | 39 | 9 | 5 | 3 | 37 | 1 | 5 | 2 |
| #3 | 35 | 10 | 12 | 4 | 29 | 1 | 6 | 2 |
| IL-10T | | | | | | | | |
| #1 | 46 | 12 | 7 | 2 | 28 | <1 | 2 | 2 |
| #2 | 56 | 19 | 4 | 1 | 18 | <1 | 1 | 1 |
| #3 | 53 | 14 | 2 | 1 | 27 | 1 | 1 | 1 |

Neu MB = neutrophilic myeloblast; Eos MB = eosinophilic myeloblast; Nuc RBC = nucleated RBC; Blast Undif. = primitive undifferentiated blastocyte The following data are the results of colony-forming assays. The assays were done with spleen cells as well as bone marrow cells, IL-3+c-kit ligand instead of IL-3+IL-6 was used to stimulate the colony-forming cells. The combination of IL-3+c-kit ligand is more effective in stimulating erythroid precursors as evidenced by comparing the numbers of BFU-e obtained in the first assay (above) with the numbers of BFU-e obtained in the following assays.

| Mice | GM | GEM | GEMM | BFU-e | CFU-e | MEG | MEG/MIX |
|---|---|---|---|---|---|---|---|
| SPLEEN (colonies/spleen) | | | | | | | |
| C1 | 18,535 | 618 | 309 | 9,268 | 42,322 | 618 | 1,236 |
| C2 | 7,736 | 893 | 595 | 2,678 | 44,926 | 1,488 | 893 |
| C3 | 8,670 | 650 | 650 | 7,152 | 71,741 | 433 | 433 |
| K1 | 55,020 | 8,400 | 3,360 | 51,660 | 393,120 | 2,100 | 6,300 |
| K2 | 111,060 | 25,746 | 10,601 | 96,925 | 498,762 | 14,135 | 12,116 |
| K3 | 68,274 | 20,096 | 9,890 | 103,050 | 1,012,633 | 14,357 | 9,252 |
| BONE MARROW (colonies/femur) | | | | | | | |
| C1 | 37,300 | 3,632 | 838 | 7,963 | 35,065 | 978 | 419 |
| C2 | 49,159 | 2,552 | 510 | 5,954 | 81,478 | 680 | 1,021 |
| C3 | 30,343 | 1,916 | 639 | 6,069 | 24,754 | 958 | 958 |
| K1 | 63,440 | 1,823 | 1,641 | 8,750 | 58,336 | 1,276 | 1,276 |
| K2 | 37,340 | 6,570 | 438 | 8,870 | 47,085 | 986 | 1,424 |
| K3 | 35,432 | 4,006 | 1,753 | 14,273 | 52,208 | 1,628 | 4,132 |

C1, C2, and C3 refer to the same control mice also designated Control #1, #2, and #3. K1, K2, and K3 refer to the same mice also designated IL-10T #1, #2, and #3.
GM = granulocyte, macrophage
GEM = granulocyte, erythoid, macrophage
GEMM = granulocyte, erythoid, macrophage, megakaryocyte

OCCULT BLOOD TESTS

| Mice | day 1 | day 2 |
|---|---|---|
| Control | | |
| #1 | neg | neg |
| #2 | neg | neg |
| #3 | no sample | neg |
| IL-10T | | |
| #1 | neg | neg |
| #2 | pos | pos |
| #3 | pos | pos |

Examination of Feces. Studies of the feces of the IL-10T mice did not reveal evidence of eggs suggesting parasitic infection. There was no evidence of mature parasites residing in the upper or lower intestine.

Conclusion. The interpretation of these results is as follows. The animals vary between slightly and markedly anemic. The anemia cannot be explained by inability to generate erythrocytes. The IL-10T mice showed signs of trying to compensate for the anemia. First, they produced larger than normal numbers of RBC precursors in their spleens. In mice, the spleen tries to compensate for RBC deficiencies, The murine spleens were two times larger than in normal animals and they were overactive in trying to generate RBC's. Some of the mice were compensating well: they had near normal numbers of RBC's in their blood and they had not released many immature cells into circulation because their reticulocyte numbers were relatively normal. However, other mice fell behind and they pushed cells into the circulation prematurely which is why their reticulocyte counts were so high (i.e., 17%). They also had a few circulating nucleated RBC's.

These mice also had higher than normal platelet counts as well as elevated numbers of megakaryocytes in their spleens. This was a sign that they may have been bleeding. Loss of blood would account for the chronic anemia with the depletion of iron stores (this iron deficiency was evident in both the spleen and bone marrow compartments). Upon autopsy, it was clear that there was no internal bleeding. However, most of the IL-10T mice showed blood in their feces and also showed prolapsed rectums. The mice were examined closely and found to be negative for pinworms, tapeworms, or other parasitic infections. There was a direct correlation between positive blood in the feces and the severity of their anemia.

In addition to the anemia and bleeding problem, the IL-10T mice had more neutrophilic granulocytes in their blood than lymphocytes. This is the opposite of what is normal for mice. See the peripheral blood differential. This observation is also consistent with the huge increase in myeloid precursors found in the spleen colony-forming assays. Thus, the mice suffered from the syndrome "anemia of chronic inflammation."

At autopsy, tissue sections prepared from IL-10T mice and litter-mate controls were examined. All specimens from the controls appeared normal. Referring to the IL-10T mice, the thymus and spinal tissue appeared normal. The spleen showed mild to marked increase in erythroblasts and myeloblasts plus megakaryocytes-RBC pools were small or essentially nonexistent. Prussian blue staining showed depletion of iron stores and there was evidence of increased extramedullary hematopoiesis. Depletion of iron stores is consistent with blood loss and results in abnormal erythropoiesis. On gross examination, the spleens were one and one-half to three times normal size. The mesenteric lymph nodes were very large compared to normal and were almost as large as a normal spleen. B and T-cell follicles were similarly enlarged, and this picture is consistent with an inflammatory response.

The small intestine showed well-formed mucosa and submucosa. In some sections, the numbers of polymorphonucleated white cells (PMN) and mononuclear cells were slightly increased. The large intestine and rectum revealed marked inflammation of the rectum extending proximally including the lower portion of the colon. A marked amount of edema and infiltrating cells were evident. PMN's were the predominant cell type, but eosinophils, lymphocytes, plasma cells, and epithelioid cells (cells which resemble epithelium) were present. Inflammation involved the mucosa, crypts and submucosa. Occasionally, infiltrates were found in the muscularis layer, especially in the internal sphincter region. In many areas, the epithelium was lost or absent. Multiple lesions showed fibrous material with aggregated RBC's and PMN's. Some blood vessels were congested with RBC's. Clumps of epithelioid cells suggested early formation of granuloma, but no well-formed granulomas were evident. There was no evidence of parasites, eggs, or intracellular bacteria. The multiple lesions and hemorrhage were consistent with the positive result of the stool occult blood test. The entire picture was consistent with IBD with secondary anemia and wasting.

2. IL-10 KO Mice Are Treated With Exogenous IL-10

Four mice which were devoid of the IL-10 gene (IL-10 KO) and three normal control mice were examined. The control mice had a normal physical appearance. All three of the control mice had negative occult blood stool samples and had normal-appearing rectums. Some of the IL-10 KO mice were noticeably smaller than the controls and they showed signs of poor health. They had ruffled hair and poor vigor compared to the normal controls. One of the four IL-10 KO mice was hunched and walked with an abnormal gait. All four of the IL-10 KO mice had swollen rectums and either erythematous rectal tissue or definite rectal prolapse. Two of the experimental KO mice had definitely positive occult blood stool samples on two separate occasions, whereas the third mouse was negative on one occasion and equivocal on a second occasion. Rectal smears were performed on all four KO mice and three had purulent exudates with large numbers of neutrophilic granulocytes. Erythrocytes were also present on individual smears of the animal was bleeding from the rectum at the time if sampling. Because IL-10 KO mice show wasting with time, the weight of the IL-10 KO mice and the normal controls were recorded as part of the examination.

Three of the IL-10 mice were injected daily for two weeks with 35 micrograms of IL-10. These three mice had consistently shown purulent exudates (only 2 out of the 3 were also showing signs of bleeding and 1 out of the 3 was hunched up and walked abnormally). One IL-10 KO mouse (negative for bleeding and a purulent exudate) and the normal controls were injected daily for two weeks with tromethamine (TRIS) buffer. The general health, physical appearance, rectal exudate, occult blood, and weight were monitored.

After the second week of IL-10 infusion, all three IL-10 KO mice showed increased vigor, smoothed hair, and normal posture and walk. All three showed reduced rectal swelling, although signs of inflammation were still present. All three had negative occult blood results and there were no signs of erythrocytes in their rectal smears. The amount of exudate was reduced; however, neutrophilic granulocytes were still observed in their rectal smears. The smear of one animal now showed more epithelial and lymphocyte cells than neutrophilic granulocytes. One animal maintained its weight at approximately 16 grams. The other two increased their weight from 16 to 17.8 grams and 11.4 to 14 grams.

The IL-10 KO mouse that received TRIS buffer for two weeks still had a negative occult blood stool sample. It now showed abundant exudate which contained large numbers of neutrophilic granulocytes. The rectum was still swollen and susceptible to prolapse. The animal was now hunched up and walked abnormally. It also showed obvious signs of wasting and its weight had dropped from 16.6 to 14 grams. The normal controls which had also been injected with TRIS buffer retained a normal health appearance including their rectums. Their occult blood stool samples were still negative and there were no rectal exudates detected. Their weight increased from 17.1 to 19 grams and 17.4 to 18.7 grams.

3. Amelioration of Signs or Symptoms of Attributable to Inflammatory Bowel Disease A human patient having IBD is treated with the invention. In particular, the patient has symptoms which may include diarrhea, abdominal pain, fever, melena, hematochezia, and weight loss and signs which may include abdominal mass, glossitis, aphthous ulcer, anal fissure, perianal fistula, anemia, malabsorption, and iron deficiency. The patient is initially treated with five $\mu$g of IL-10 per kilogram body weight per day. Because the patient weighs 70 kg, the initial starting dose is 350 $\mu$g per day of IL-10. This dose is administered as an intravenous bolus. The dose is increased by about 50 to 150 $\mu$g per day depending on the patient's tolerance and response. An optimum dose of about 700 $\mu$g per day (10 $\mu$g per kilogram per day) is achieved after several days.

Prior to the first treatment, and daily thereafter until several days after the final treatment, the patient is monitored clinically and with laboratory parameters. The laboratory parameters include blood counts with particular attention to the total white blood cell count and its differential. Of special interest is whether the amount of white cells remains normal or without significant change from the patient's pre-treatment level. With respect to the white cell differential, particular attention is given to whether immature forms are appearing in the peripheral blood and whether the normal ratio of different types of white cells is constant or changing. Special attention is paid to the ratio of lymphocytes and monocytes in the peripheral blood.

Additional parameters which can be monitored include the erythrocyte sedimentation rate (ESR), chemical profiles, blood levels of IL-6, TNF and IFN-$\gamma$. Finally, regular, such as daily, evaluation of the patient's stool for blood and purulent exudate can indicate the patient's response to therapy.

All of the references refered to herein are incorporated by reference. Additionally, other aspects of the invention will be readily apparent to those of ordinary skill in the art. Thus, the invention is not limited by the preceding description and examples, but rather by the claims that follow.

What is claimed is:

1. A method of treating an inflammatory bowel disease in a mammal comprising:
   administering to the mammal an effective amount of IL-10.

2. The method of claim 1 wherein the inflammatory bowel disease is Crohn's Disease.

3. The method of claim 1 wherein the inflammatory bowel disease is ulcerative colitis.

4. The method of claim 1 wherein the administration is parenteral.

5. The method of claim 4 wherein the parenteral administration is intravenous.

6. The method of claim 1 wherein the effective amount is selected from a range of about 1 microgram to about 100 milligrams per kilogram of body weight.

7. The method of claim 6 wherein the effective amount is selected from a range of about 10 micrograms to about 1000 micrograms per kilogram of body weight.

8. The method of claim 6 wherein the effective amount is selected from a range of about 50 micrograms to about 100 micrograms per kilogram of body weight.

9. The method of claim 1 wherein the mammal is a human.

10. The method of claim 4 further comprising using combination therapy including co-administration of effective amounts of IL-10 and at least one additional therapeutic agent.

11. The method of claim 10 wherein the additional therapeutic agent is selected from a group consisting of corticosteroids, sulphasalazine, cyclosporin A, mercaptopurine, and azathioprine.

12. The method of claim 10 wherein the co-administration is sequential.

13. The method of claim 10 wherein the co-administration is simultaneous.

14. A method of predicting a mammal's predisposition for development of an inflammatory condition associated with inflammatory bowel disease characterized by suboptimal levels of IL-10 comprising:
   1) assaying a sample taken from the mammal for an IL-10 level and 2) comparing the IL-10 level in the sample to a known normal value of IL-10.

15. The method of claim 14 wherein the sample is blood.

16. The method of claim 14 wherein the inflammatory condition is selected from a group consisting of an inflammatory bowel disease, an anemia associated with an inflammatory bowel disease, an arthritis associated with an inflammatory bowel disease, and a dermatitis associated with an inflammatory bowel disease.

17. The method of claim 16 wherein the inflammatory bowel disease is selected from a group consisting of ulcerative colitis and Crohn's Disease.

18. A pharmaceutical composition for administration to a mammal having an inflammatory bowel disease comprising:
   an effective amount of IL-10 to ameliorate at least one of a symptom or a sign of the inflammatory bowel disease in the mammal; and
   a pharmaceutically acceptable additive.

19. The composition of claim 19 wherein the amount of IL-10 is selected from a range of about 1 microgram to about 100 milligrams per kilogram of body weight of the mammal.

20. The composition of claim 18 wherein the composition is in a form suitable for parenteral administration.

21. The composition of claim 18 wherein the pharmaceutically acceptable additive is an aqueous vehicle.

22. The composition of claim 18 wherein the effective amount is a unit dose presented in an ampoule.

23. The composition of claim 18 wherein the inflammatory bowel disease is selected from a group consisting of ulcerative colitis and Crohn's Disease.

24. The composition of claim 18 wherein the symptom is selected from a group consisting of diarrhea, abdominal pain, fever, melena, hematochezia, and weight loss.

25. The composition of claim 18 wherein the sign is selected from a group consisting of abdominal mass, glossitis, aphthous ulcer, anal fissure, perianal fistula, anemia, malabsorption, and iron deficiency.

* * * * *

UNITED STATES PATENT AND TRADEMARK OFFICE
CERTIFICATE OF CORRECTION

PATENT NO. : 5,368,854
DATED : November 29, 1994
INVENTOR(S) : Donna Rennick

It is certified that error appears in the above-indentified patent and that said Letters Patent is hereby corrected as shown below:

Column 1, line 2, insert the word --THE-- before the word "USE".

Column 13, second table titled BONE MARROW DIFFERENTIALS, each number under the heading Plasma cell for rows #1, #2, and #3 under Control, "1" should read --<1--.

Column 13, line 36, "bone marrow cells," should be --bone marrow cells.--.

Column 15, line 6, "RBC deficiencies," should be --RBC deficiencies.--.

Column 15, line 44, "megakaryocytes-" should be --megakaryocytes.--.

Column 18, line 4, "claim 6" should be --claim 7--.

UNITED STATES PATENT AND TRADEMARK OFFICE
CERTIFICATE OF CORRECTION

PATENT NO. : 5,368,854                        Page 2 of 2
DATED : November 29, 1994
INVENTOR(S) : Donna Rennick It is certified that error appears in the above-indentified patent and that said Letters Patent is hereby corrected as shown below:

Column 18, line 46, "claim 19" should be —claim 18—.

Signed and Sealed this

Twenty-fifth Day of April, 1995

Attest:

BRUCE LEHMAN

Attesting Officer        Commissioner of Patents and Trademarks